United States Patent [19]

Peglion et al.

[11] Patent Number: 5,684,020
[45] Date of Patent: Nov. 4, 1997

[54] PIPERAZINE, PIPERIDINE AND 1,2,5,6-TETRAHYDROPYRIDINE

[75] Inventors: Jean-Louis Peglion, Le Vesinet; Aimée Dessinges, Thiais; Bertrand Goument, Viroflay; Mark Millan, Paris; Adrian Newman-Tancredi, Le Pecq; Alain Gobert, Saint Denis, all of France

[73] Assignee: Adir et Compagnie, Courbevoie, France

[21] Appl. No.: 792,179

[22] Filed: Jan. 30, 1997

Related U.S. Application Data

[62] Division of Ser. No. 655,457, May 30, 1996.

[30] Foreign Application Priority Data

May 31, 1995 [FR] France .................... 95 06436

[51] Int. Cl.$^6$ ............... A61K 31/445; C07D 405/04; C07D 407/14
[52] U.S. Cl. .................... 514/320; 514/321; 514/324; 514/254; 544/367; 544/376; 544/377; 546/196; 546/197; 546/202
[58] Field of Search .................... 546/196, 197, 546/202; 514/320, 321, 324

[56] References Cited

U.S. PATENT DOCUMENTS

| 3,377,347 | 4/1968 | Jenny et al. | 260/247 |
| 5,232,931 | 8/1993 | Prucher et al. | 514/321 |

*Primary Examiner*—Mukund J. Shah
*Assistant Examiner*—Brenda Coleman
*Attorney, Agent, or Firm*—The Firm of Gordon W. Hueschen

[57] ABSTRACT

A compound selected from those of formula:

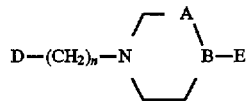

wherein:
A–B, n, D and E are as defined in the specification,
their racemic mixtures, and their optical isomers,
and also the physiologically tolerable salts thereof with appropriate acids.

The products of the invention may be used therapeutically.

6 Claims, No Drawings

PIPERAZINE, PIPERIDINE AND 1,2,5,6-TETRAHYDROPYRIDINE

The present application is a division of our prior-filed copending application Ser. No. 08/655,457, filed May 30, 1996, now pending.

The present invention relates to new piperazine, piperidine and 1,2,5,6-tetrahydropyridine compounds.

It relates more especially to compounds of formula I:

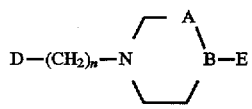

wherein

A–B is selected from the group consisting of: $CH_2$—CH, CH=C and $CH_2$—N, n is selected from the group consisiting of zero and integers of from 1 to 6 inclusive, D represents one of the following bicyclic systems:

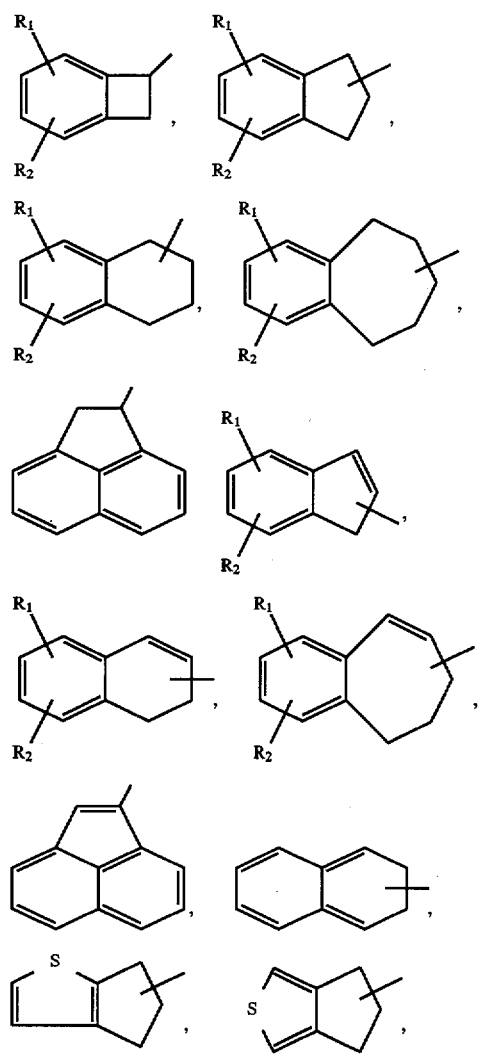

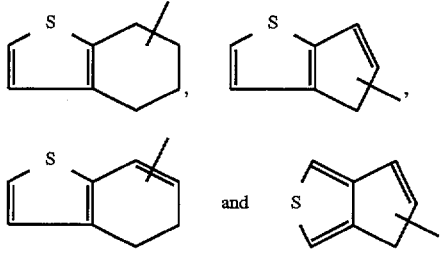

wherein:

$R_1$ and $R_2$, which are identical or different, are each selected from the group consisting of hydrogen and halogen atoms, straight-chain and branched alkyl and alkoxy radicals each having from 1 to 5 carbon atoms inclusive and a hydroxy radical; and E represents one of the following heterocycles:

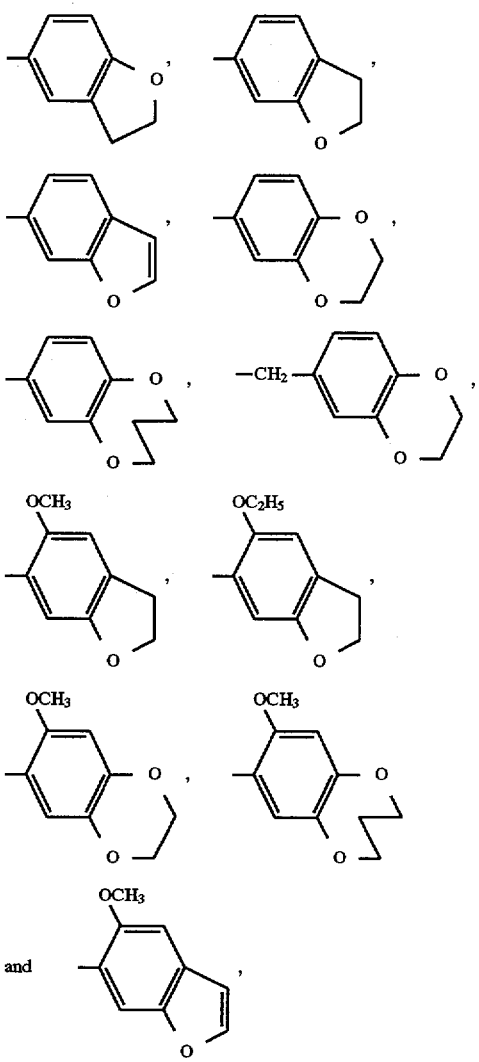

but with the proviso that E does not represent:

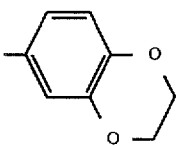

when D is selected from the group consisting of

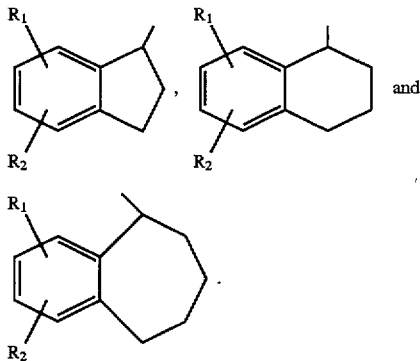

The presence of asymmetric carbon atoms implies that the molecules of the invention exist in the form of a racemic mixture or racemate and optical isomers or enantiomers, which are also included in the present invention. Furthermore, the compounds of the invention may form, with pharmaceutically acceptable acids, mineral or organic acid salts to which the present invention also relates.

The dopaminergic system is implicated in a significant number of disorders of the central nervous system that are associated either with a hyperactivity (such as, for example, schizophrenia) or with a hypoactivity (such as, for example, Parkinson's disease) of that system. Depression, impulse disorders and memory disorders also belong to the illnesses for which it has been possible to demonstrate the part played by dopamine in their etiology. Until now, treatment of those illnesses has been ensured by $D_2$ dopaminergic blockers (for disorders associated with hyperactivity) and by $D_2$ dopaminergic activators (for disorders associated with hypoactivity). However, treatments with conventional neuroleptics, which are $D_2$ dopaminergic receptor blockers, have numerous side effects: tardive dyskinesia, malignant neuroleptic syndrome, hyperprolactinaemia and amenorrhoea. In addition, $D_2$ dopaminergic receptor stimulants cause nausea and troublesome motor and cardiovascular side effects. Recently, three other dopaminergic receptors have been discovered in addition to the already known $D_1$ and $D_2$ receptors: $D_3$ (P. Sokoloff et al, Nature, 1990, 347, 147), $D_4$ (Van Tol et al, Nature, 1991, 350, 610) and $D_5$ (Sunhara et al, Nature, 1991, 350, 614). The present invention relates more especially to $D_4$ receptor agonist or antagonist ligands that possess a high selectivity in relation to other dopaminergic receptors, especially $D_2$ receptors, giving those products valuable therapeutic properties because of the relative absence of $D_4$ receptor in the hypophysis and in the basal ganglia structures and without, at the same time, the known side effects of $D_2$ ligands.

It should also be mentioned that an increase of cortical dopaminergic transmission plays a key role in the treatment of the deficient symptoms of schizophrenia.

The closest prior art to the present invention relates to 1-(2,3-dihydro-1,4-benzodioxin-6-yl)-piperazine compounds, described in the patent specifications U.S. Pat. No. 5,242,925 (serotonin agonists/antagonists), EP 0 300 908 (anti-arrhythmics), EP 0 072 960 and EP 0 072 961 (anti-allergics). Those patent specifications nowhere either include or suggest the compounds forming the object of the present invention and could not influence the patentability of the present Application.

The compounds of the present invention thus differ from the compounds of the prior art not only in their chemical structure but also in respect of their pharmacological and therapeutic activities. Those activities have been demonstrated:
in vitro
by cloned human $D_2$ and $D_4$ receptor binding studies
and
in vivo
a) using pharmacological models:
by dopamine synthesis (turnover) studies in the following structures: frontal cortex (mesocortical pathway), nucleus accumbens and olfactory tubercle (mesolimbic pathway), striatum (nigrostriatal pathway). The functional dopaminergic antagonists cause an increase in the synthesis of dopamine in those structures.
by dialysis studies in the structures mentioned above, during the course of which the products of the invention are characterised as a function of their effects on dopaminergic, noradrenergic or seretoninergic activity.
A selective increase in the release of dopamine in the frontal cortex compared with the nucleus accumbens and the striatum makes it possible to forecast therapeutic effects of an antidepressant, antipsychotic and promnesic type.

The above activities have been confirmed.
b) using therapeutic models:
and especially using the following tests:
the inhibition of verticalisation induced by apomorphine in mice (antipsychotic properties)
the inhibition of aggressiveness in isolated mice (anti-impulse and anxiolytic properties).

On the other hand, the absence of side effects has been demonstrated especially by an absence of activity in
the catalepsy induction test in the rat.

Thus, in their activity as selective ligands of $D_4$ receptors, the products of the invention may be used in the prevention of, or in disorders associated with, a dysfunction of the dopaminergic system. More especially, their usefulness as antipsychotics and anti-depressants in the treatment of impulse disorders and memory disorders, and as anxiolytics, is claimed in relation to their activity in the tests mentioned above.

The invention relates also to a process for the preparation of compounds of formula I which is characterised in that:

a compound of formula II:

(II)

wherein A–B and E are as defined above, is condensed with a compound of formula III:

(III)

wherein n and D are as defined above and X represents a halogen atom or a mesyloxy or tosyloxy radical.

The condensation is carried out especially suitably in an appropriate solvent, such as, for example, methyl ethyl ketone, methyl isobutyl ketone, toluene, dimethylformamide or dimethyl acetamide, in the presence of an acceptor for the acid formed during the course of the reaction, at a temperature of from 20° to 150° C. There may be used as acceptor, for example, an alkali metal carbonate, such as sodium carbonate, or a tertiary amine, such as triethylamine.

Furthermore, compounds of formula I wherein n has a meaning other than zero, that is to say compounds corresponding more precisely to formula I':

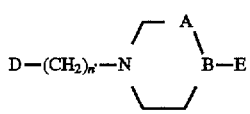

wherein A—B, D and E are as defined above and n' represents an integer of from 1 to 6, have also been prepared in accordance with a variant of the above process which is characterised in that:

a compound of formula II defined above
is condensed with
a compound of formula IV:

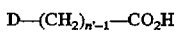

wherein:
D and n' are as defined above,
and the amide so obtained of formula V:

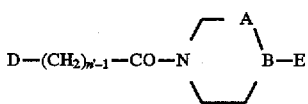

wherein
A—B, D, E and n' are as defined above, is reduced.

The condensation of compounds II and IV is especially suitably carried out in an appropriate solvent, such as, for example, methylene chloride, in the presence of carbonyldiimidazole.

The reduction of amide V is advantageously carried out by means of a lithium aluminium hydride in ether or tetrahydrofuran or by means of borane-dimethyl sulphide in tetrahydrofuran, or sodium alkoxyaluminohydride in toluene such as Red Al®.

The latter process for the preparation of compounds I' is also included in the present invention.

In addition, the amides of formula V are new intermediate products which, as such, form part of the present invention.

The starting materials of formulae II, III and IV are either known products, or products prepared from known compounds in accordance with known processes, as specified in the Examples hereinafter.

The compounds of formula I yield salts with physiologically tolerable acids. Those salts are also included in the present invention.

The present invention relates also to pharmaceutical compositions comprising as active ingredient a compound of the general formula I or a physiologically tolerable salt thereof, mixed with or in association with an appropriate pharmaceutical excipient, such as, for example, glucose, lactose, talc, ethyl cellulose, magnesium stearate or cocoa butter. The pharmaceutical compositions so obtained are generally presented in dosage form and may contain from 0.1 to 100 mg of active ingredient. They may, for example, be in the form of tablets, dragées, gelatin capsules, injectable or drinkable solutions and, depending on the case in question, may be administered by the oral, rectal or parenteral route at a dose of from 0.1 to 100 mg of active ingredient from 1 to 3 times per day.

The following Examples illustrate the present invention, melting points being determined with a Kofler hot plate (K), where required under microscope (M.K.).

EXAMPLE 1

1-(Benzocyclobutan-1-ylmethyl)-4-(2,3-dihydrobenzo-1,4-dioxin-6-yl)piperazine

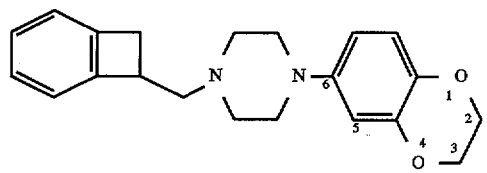

2.26 g (7.8×10-3 mol) of 1-hydroxymethylbenzocyclobutane tosylate, 1.7 g (7.8×10-3 mol) of 4-(2,3-dihydrobenzo-1,4-dioxin-6-yl) piperazine and 2.16 g (15.6×10-3 mol) of K2CO3 in 50 ml of methyl isobutyl ketone are mixed together. That mixture is heated at 100° C. for 8 hours and then cooled. The mixture is concentrated and the residue is taken up in water and ethyl acetate. Separation is carried out and the organic phase then extracted with 1N HCl. The aqueous phase is rendered basic with 1N NaOH and then extracted with methylene chloride and dried over MgSO4. The oil obtained is purified by flash chromatography (eluant CH2Cl2/CH3OH: 95/5). 1 g (yield= 38%) of an oil that corresponds to the title compound is obtained, the dihydrochloride of which is prepared in acetonitrile. M.p. 242°–245° C.

EXAMPLE 2

4-(2,3-Dihydrobenzo-1,4-dioxin-6-yl)-1-(indan-2-yl) piperazine

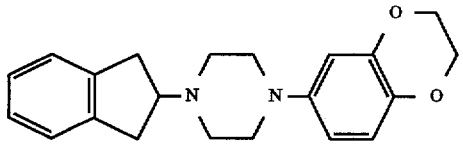

Prepared in the same manner as in Example 1, but using indan-2-ol tosylate instead of 1-hydroxymethylbenzocyclobutane tosylate, the title compound obtained melts at 183°–185° C.

EXAMPLE 3

1-[2-(Benzocyclobutan-1-yl)ethyl]-4-(2,3-dihydro-5-methoxybenzofuran-6-yl)piperazine

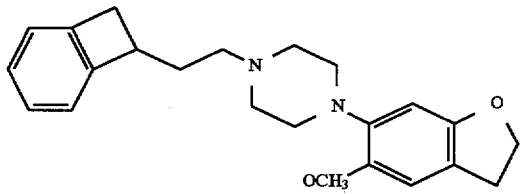

2.21 g (8.2 mmol) of 4-(2,3-dihydro-5-methoxybenzofuran-6-yl)piperazine (Preparation 1), 1.72 g (8.2 mmol) of 2-(benzocyclobutan-1-yl)-1-bromoethane and 3.48 g (32.8 mmol) of sodium carbonate in 33 ml of methyl isobutyl ketone are heated at reflux for 14 h. The whole is evaporated to dryness, taken up in 200 ml of ethyl acetate and 100 ml of N sodium hydroxide solution and decanted, and the organic phase is washed with 100 ml of a saturated sodium chloride solution. After drying over $MgSO_4$ and evaporation, the residue obtained is chromatographed on silica (eluant: $CH_2Cl_2/CH_3OH$: 98/2) to yield 2.1 g of the expected product. By the addition of a 2% fumaric acid solution in ethanol, 1.7 g of the fumarate of the title compound is obtained. M.p. 193°–194° C.

EXAMPLE 4

1-(2,3-Dihydro-5-methoxybenzofuran-6-yl)-4-[2-(naphth-1-yl)ethyl]piperazine

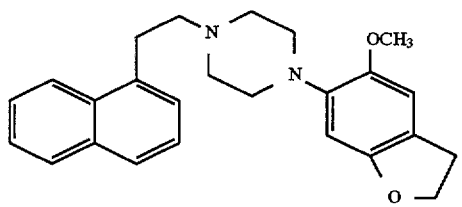

Prepared in the same manner as the product of Example 3 but using 2-(naphth-1-yl)-1-bromoethane instead of 2-(benzocyclobutan-1-yl)-1-bromoethane.

The resulting fumarate of the title compound melts at 177°–179° C. after recrystallisation from ethanol.

EXAMPLE 5

4-[2-(Benzocycloheptan-1-yl)ethyl]-1-(2,3-dihydro-5-methoxybenzofuran-6-yl)piperazine

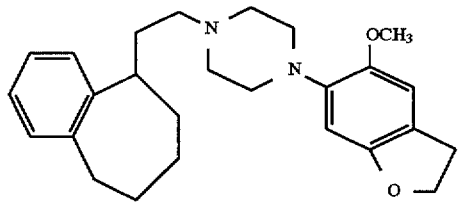

Prepared in the same manner as the product of Example 3 but using 2-(benzocycloheptan-1-yl)ethanol mesylate instead of 2-(benzocyclobutan-1-yl)-1-bromoethane.

The resulting fumarate of the title compound melts at 225°–227° C. after recrystallisation from ethanol.

EXAMPLE 6

4-(2,3-Dihydrobenzo-1,4-dioxin-6-yl)-1-(indan-2-ylmethyl)piperazine

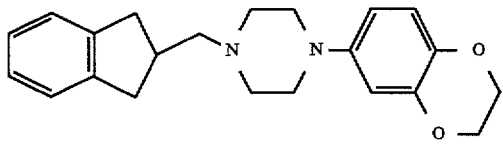

Step 1. "Amide"

Add 4.9 g (29.5 mmol) of carbonyldiimidazole in one go to 4.9 g (29.5 mmol) of indan-2-ylcarboxylic acid dissolved in 50 ml of methylene chloride. The reactants are left in contact for one hour after the evolution of gas has ceased, then 6.4 g (29.5 mmol) of 4-(2,3-dihydrobenzo-1,4-dioxin-6-yl)piperazine dissolved in 50 ml of methylene chloride is rapidly added dropwise. The reactants are left in contact overnight, transferred to a separating funnel and extracted with 1N HCl. The acidic phases are rendered basic cold and extracted with ethyl acetate. 8.3 g of the expected amide (yield=69%) are obtained, which are used without being purified.

Step 2. Title compound

A solution of 8 g (21.9 mmol) of the amide obtained above in 100 ml of THF is poured into 0.8 g of $LiAlH_4$ suspended in 30 ml of THF. The reactants are left in contact overnight and the mixture is decomposed in succession with $H_2O$ (0.54 ml), 20% NaOH (0.44 ml) and $H_2O$ (2 ml). The precipitate is filtered, washed with THF and evaporated to obtain an oil that corresponds to the desired product. By means of the slow addition of an ethereal hydrogen chloride solution to the base dissolved in acetonitrile, 1.5 g of the dihydrochloride of the title compound are obtained. M.p.: 220°–222° C.

EXAMPLE 7

1-(Indan-2-ylmethyl)-4-(2,3-dihydro-5-methoxybenzofuran-6-yl)piperazine

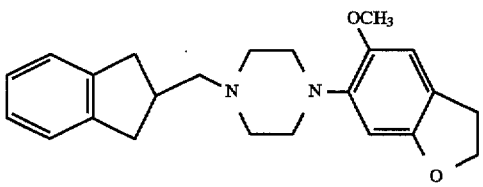

The title compound was obtained in the same manner as the product of Example 6, but with the use in Step 1 of 4-(2,3-dihydro-5-methoxybenzofuran-6-yl)piperazine (Preparation 1) instead of 4-(2,3-dihydrobenzo-1,4-dioxin-6-yl)piperazine. The hydrochloride of the title compound, obtained by the slow addition of an ethereal hydrogen chloride solution to the base dissolved in ether, melts at 201°–204° C.

EXAMPLE 8

4-[2-(Benzocyclohept-1-en-1-yl)ethyl]-1-(2,3-dihydro-5-methoxybenzofuran-6-yl)piperazine

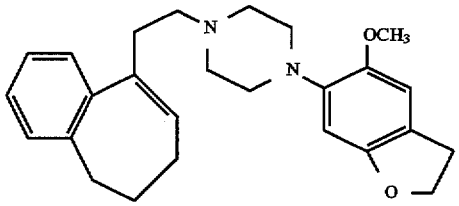

Obtained in the same manner as the product of Example 6 but with the use in Step 1 of 4-(2,3-dihydro-5-methoxybenzofuran-6-yl)piperazine instead of 4-(2,3-dihydrobenzo-1,4-dioxin-6-yl)piperazine on the one hand, and 2-(benzocyclohept-1-en-1-yl)acetic acid instead of indan-2-ylcarboxylic acid on the other hand.

The fumarate of the title compound melts at 207°–209° C. after recrystallisation from ethanol.

EXAMPLE 9

1-[2-(Benzocyclobutan-1-yl)ethyl]-4-(2,3-dihydrobenzo-1,4-dioxin-6-yl)piperazine

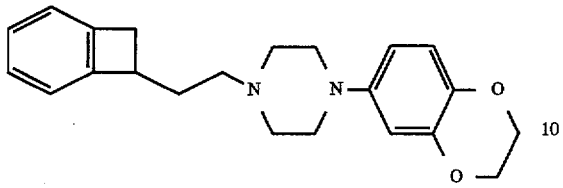

Step 1. "Amide"

Identical to Step 1 of Example 6 but using benzocyclobutan-1-ylacetic acid instead of indan-2-ylcarboxylic acid.

Step 2. Title compound 7.92 ml (79.2 mmol) of borane-dimethyl sulphide are added dropwise to 7.9 mmol of the amide obtained above in 150 ml of anhydrous THF. The whole is heated at reflux for 6 hours. After returning to room temperature, the mixture is decomposed by pouring in dropwise 16 ml of methanol and then heating at reflux for 3 hours. After evaporation of the solvents an oil is obtained that corresponds to the title compound (yield=93%). The hydrochloride melts at 200°–204° C.

EXAMPLE 10

1-[3-(Benzocyclobutan-1-yl)propyl]-4-(2,3dihydrobenzo-1,4-dioxin-6-yl)piperazine

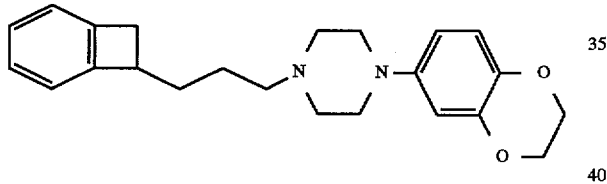

Prepared in the same manner as the title compound of Example 9 but using the method of operation of Step 1 of Example 6, in which indan-2-ylcarboxylic acid has been replaced by 3-(benzocyclobutan-1-yl)propionic acid, to prepare the amide (yield=79%). The dihydrochloride melts at 196°–199° C.

EXAMPLE 11

4-(2,3-Dihydrobenzo-1,4-dioxin-6-yl)-1-(indan-2-ylmethyl)piperidine

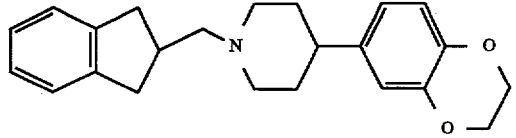

Step 1. "Amide"

Identical to Step 1 of Example 6 but using 4-(2,3-dihydrobenzo-1,4-dioxin-6-yl)piperidine (Preparation 2) instead of 4-(2,3-dihydrobenzo-1,4-dioxin-6-yl)piperazine. After flash chromatography on silica with an eluant composed of the mixture $CH_2Cl_2/CH_3COOC_2H_5$: 95/5, the expected amide is obtained in a yield of 61%.

Step 2. Title compound

Identical to Step 2 of Example 9. The dihydrochloride of the title compound melts at 218°–220° C. (yield=42%).

EXAMPLE 12

1-(2,3-Dihydro-5-methoxybenzofuran-6-yl)-4-[2-(1,2,3,4-tetrahydronaphthalen-1-yl)ethyl]piperazine

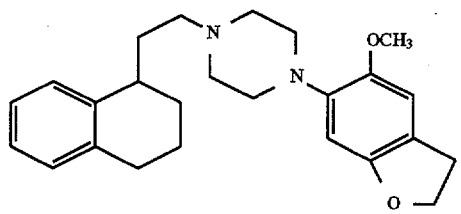

Prepared as described in Example 9, starting from 1,2,3,4-tetrahydronaphthalen-1-ylacetic acid and 4-(2,3-dihydro-5-methoxybenzofuran-6-yl)piperazine. The fumarate of the title compound melts at 219°–220° C. after recrystallisation from ethanol.

EXAMPLE 13

1-(2,3-Dihydro-5-ethoxybenzofuran-6-yl)-4-[2-(indan-2-yl)methyl]piperazine

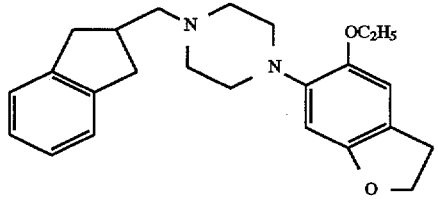

Prepared as described in Example 9, starting from 4-(2,3-dihydro-5-ethoxybenzofuran-6-yl)piperazine (Preparation 4). The fumarate of the title compound melts at 183°–185° C. (ethanol).

EXAMPLE 14

1-[3-(Benzocyclobutan-1-yl)propyl]-4-(benzo-1,5-dioxepin-7-yl)piperazine

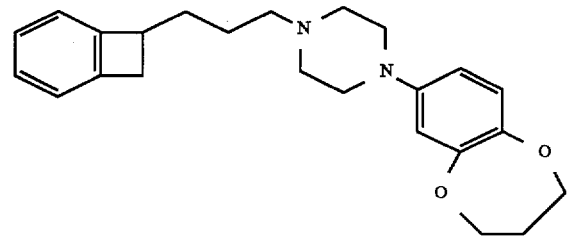

Prepared as described in Example 9, starting from 3-(benzocyclobutan-1-yl)propionic acid and 4-(benzo-1,5-dioxepin-7-yl)piperazine. The fumarate of the title compound melts at 168°–170° C. (ethanol).

EXAMPLE 15

4-(Benzo-1,5-dioxepin-7-yl)-1-[(indan-2-yl)methyl]piperazine

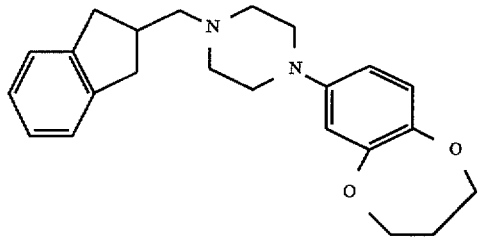

Prepared as described in Example 9, starting from 4-(benzo-1,5-dioxepin-7-yl)piperazine. The hemi-fumarate of the title compound melts at 179°–181° C. (ethanol).

EXAMPLE 16

4-[(2,3-Dihydrobenzo-1,4-dioxin-6-yl)methyl]-1-[(indan-2-yl)methyl]piperazine

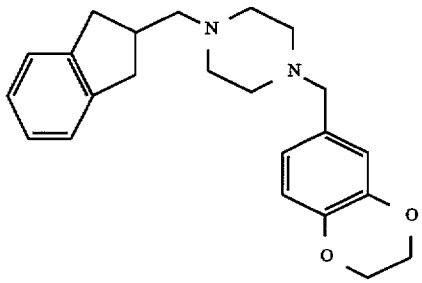

Prepared as described in Example 9, starting from 4-[(2,3-dihydrobenzo-1,4-dioxin-6-yl)methyl]piperazine. The difumarate of the title compound melts at 217°–220° C. (ethanol).

EXAMPLE 17

4-[(2,3-Dihydro-5-methoxybenzofuran-6-yl)]-1-(4,5,6,7-tetrahydrobenzo[b]thien-5-yl)methyl]piperazine

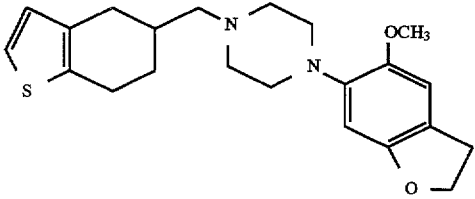

Prepared as described in Example 9, starting from 4,5,6,7-tetrahydrobenzo[b]thien-5-ylcarboxylic acid and 4-(2,3-dihydro-5-methoxybenzofuran-6-yl)piperazine. The fumarate of the title compound metls at 198°–200° C. (ethanol).

EXAMPLE 18

1-(2,3-Dihydrobenzo-1,4-dioxin-6-yl)-4-[2-(naphth-1-yl)ethyl]piperazine

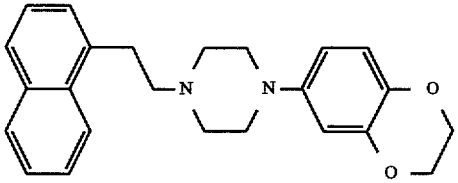

Prepared as described in Example 9, starting from naphth-1-ylacetic acid. The dihydrochloride of the title compound melts at 223°–232° C. (methanol).

EXAMPLE 19

1-[(Cyclopenta[b]thien-5-yl)methyl]-4-(2,3dihydro-5-methoxybenzofuran-6-yl)piperazine

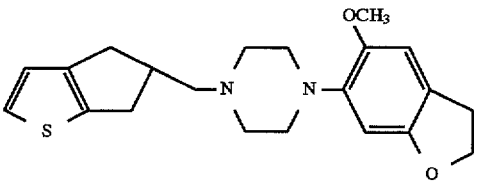

Prepared as described in Example 9, starting from (cyclopenta[b]thien-5-yl)carboxylic acid (Preparation 8) and 4-(2,3-dihydro-5-methoxybenzofuran-6-yl)piperazine. The fumarate of the title compound melts at 186°–190° C. (ethanol).

EXAMPLE 20

1-[(Cyclopenta[c]thien-5-yl)methyl]-4-(2,3-dihydro-5-methoxybenzofuran-6-yl)piperazine

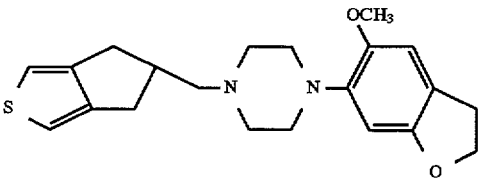

Prepared as described in Example 9, starting from (cyclopenta[c]thien-5-yl)carboxylic acid (Preparation 7) and 4-(2,3-dihydro-5-methoxybenzofuran-6-yl)piperazine. The title compound melts at 156°–158° C.

EXAMPLE 21

4-(2,3-Dihydrobenzo-1,4-dioxin-6-yl)-1-[2-(naphth-1-yl)ethyl]piperidine

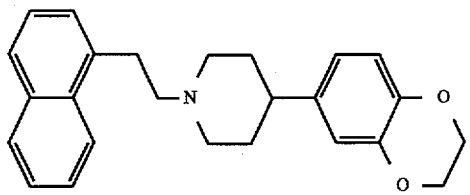

Prepared as described in Example 11 but with the use in Step 1 of naphth-1-ylacetic acid instead of indan-2-ylcarboxylic acid. The hydrochloride of the title compound melts at 220°–223° C. (methyl cyanide).

EXAMPLE 22

1-[(Acenaphthen-1-yl)methyl]-4-(2,3-dihydro-5-methoxybenzofuran-6-yl)piperazine

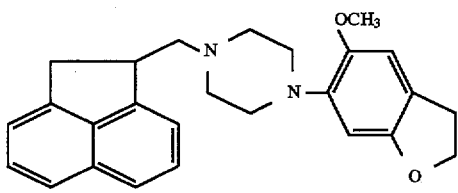

Prepared as described in Example 9, starting from acenaphthen-1-ylcarboxylic acid and 4-(2,3-dihydro-5-methoxybenzofuran-6-yl)piperazine. The fumarate of the title compound melts at 226°–228° C. (ethanol).

EXAMPLE 23

4-(2,3-Dihydro-7-methoxybenzo-1,4-dioxin-6-yl)-1-[(indan-2-yl)methyl]piperazine

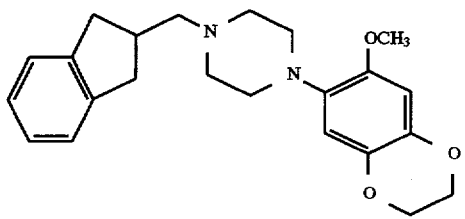

Prepared as described in Example 9, starting from 4-(2,3-dihydro-7-methoxybenzo-1,4-dioxin-6-yl)piperazine (Preparation 5). The fumarate of the title compound melts at 176°–178° C. (ethanol).

EXAMPLE 24

4-(2,3-Dihydrobenzo-1,4-dioxin-6-yl)-1-[(1,2,3,4-tetrahydronaphth-2-yl)methyl]piperazine

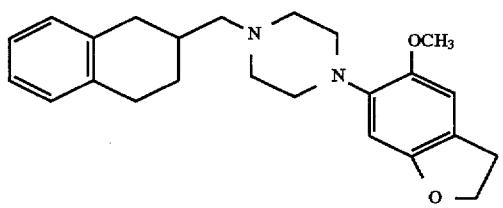

Prepared as described in Example 9, starting from 1,2,3,4 tetrahydronaphth-2-ylcarboxylic acid. The hydrochloride of the title compound melts at 226°–229° C. (methanol).

EXAMPLE 25

4-(2,3-Dihydro-5-methoxybenzofuran-6-yl)-4-[(1,2,3,4-tetrahydronaphth-2-yl)methyl]piperazine

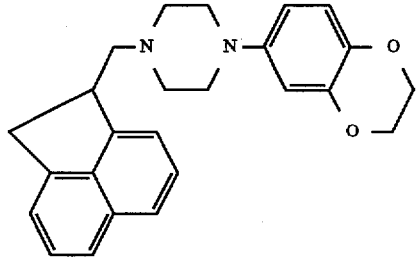

Prepared as described in Example 9, starting from 1,2,3,4-tetrahydronaphth-2-ylcarboxylic acid and 4-(2,3-dihydro-5-methoxybenzofuran-6-yl)piperazine. The fumarate of the title compound melts at 219°–221° C. (ethanol).

EXAMPLE 26

1-(Acenaphthen-1-ylmethyl)-4-(2,3-dihydrobenzo-1,4-dioxin-6-yl)piperazine

Prepared as described in Example 9, starting from acenaphthen-1-ylcarboxylic acid. The hydrochloride of the title compound melts at 192°–196° C. (ether).

EXAMPLE 27

1-[(Indan-2-yl)methyl]-4-(8-methoxybenzo-1,5-dioxepin-7-yl)piperazine

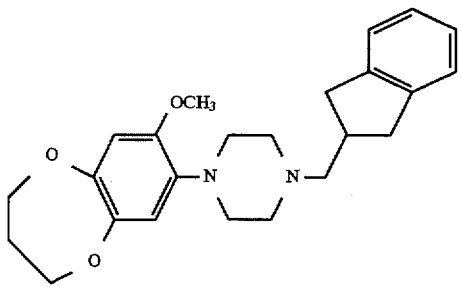

Prepared as described in Example 9, starting from 4-(8-methoxybenzo-1,5-dioxepin-7-yl)-piperazine (Preparation 6). The title compound melts at 120°–122° C. (ethanol).

EXAMPLE 28

4-(2,3-Dihydrobenzofuran-5-yl)-1-(indan-2-ylmethyl)piperazine

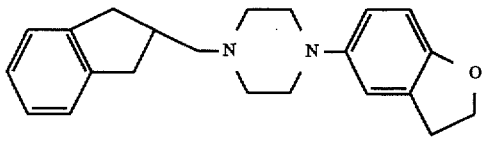

Prepared as described in Example 9, starting from 4-(2,3-dihydrobenzofuran-5-yl)-piperazine. The fumarate of the title compound melts at 180°–182° C. (ethanol).

EXAMPLE 29

4-(2,3-Dihydro-5-methoxybenzofuran-6-yl)-1-(indan-1-ylmethyl)piperazine

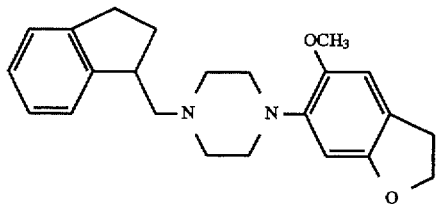

Prepared as described in Example 9, starting from indan-1-ylcarboxylic acid and 4-(2,3-dihydro-5-methoxybenzofuran-6-yl)piperazine. The fumarate of the title compound melts at 195°–197° C. (ethanol).

EXAMPLE 30

4-(2,3-Dihydrobenzofuran-6-yl)-1-(indan-2-ylmethyl)piperazine

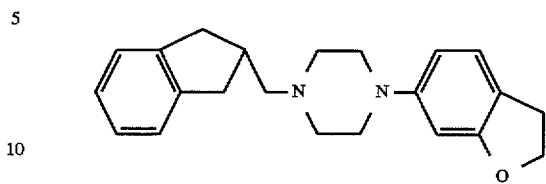

Prepared as described in Example 9, starting from 4-(2,3-dihydrobenzofuran-6-yl)-piperazine. The hemi-fumarate of the title compound melts at 171°–173° C. (ethanol).

EXAMPLE 31

4-(2,3-Dihydrobenzo-1,4-dioxin-6-yl)-1-[(indan-2-yl)methyl]-1,2,3,6-tetrahydropyridine

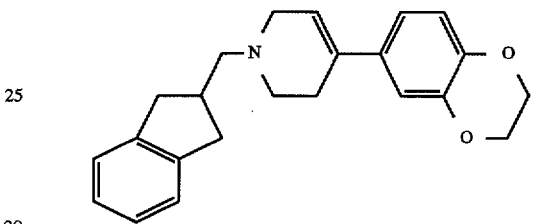

Step 1: "Amide"

Identical to Step 1 of Example 6, but using 4-(2,3-dihydrobenzo-1,4-dioxin-6-yl)-1,2,3,6-tetrahydropyridine (Preparation 3) instead of 4-(2,3-dihydrobenzo-1,4-dioxin-6-yl)-piperazine.

Step 2: Title compound 4.4 ml (15.8 mmol) of Red-Al® 3.5M in toluene, are poured dropwise into a solution of 1.9 g (5.2 mmol) of the amide prepared above in 60 ml of toluene. The whole is heated for 2 hours at 50° C. and then stirred overnight at room temperature. The whole is then cooled with an ice bath and hydrolysed in succession with 2.2 ml of ethanol and 2.6 ml of water. The aluminium salts are filtered off and the filtrate is evaporated to dryness. 1.4 g of an oil is obtained which is purified by flash chromatography.

The fumarate of the title compound melts at 160°–167° C. (ethanol).

Yield: 25%

EXAMPLE 32

4-(2,3-Dihydrobenzo-1,4-dioxin-6-yl)-1-[2-(naphth-1-yl)ethyl]-1,2,3,6-tetrahydropyridine

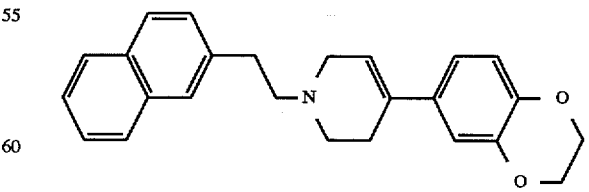

Prepared as described in Example 28, but with the use in Step 1 of naphth-1-ylacetic acid instead of indan-1-ylcarboxylic acid. The fumarate of the title compound melts at 170°–180° C. (ethanol).

EXAMPLE 33

4-(2,3-Dihydro-5-methoxybenzofuran-6-yl)-1-[2-(1,2-dihydronaphthalen-3-yl)methyl]-piperazine

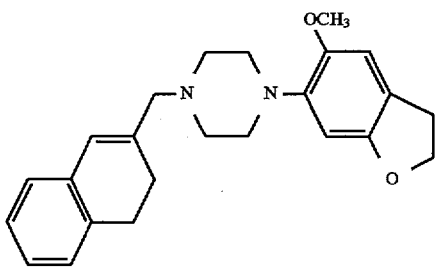

Prepared as described in Example 31, but in Step 1 using 1,2-dihydronaphthalen-3-ylcarboxylic acid and 4-(2,3-dihydro-5-methoxybenzofuran-6-yl)piperazine. The fumarate of the title compound melts at 180°–184° C. (ethanol).

EXAMPLE 34

1-(Indan-2-ylmethyl)-4-(5-methoxybenzofuran-6-yl)piperazine

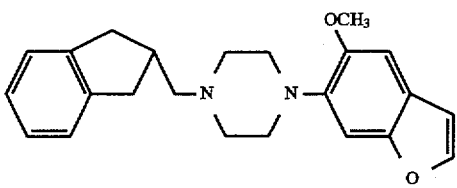

Prepared as described in Example 31, but in Step 1 using 4-(5-methoxybenzofuran-6-yl)piperazine. The fumarate of the title compound melts at 188°–192° C. (ethanol).

EXAMPLE 35

4-(Benzofuran-6-yl)-1-(indan-2-ylmethyl)piperazine

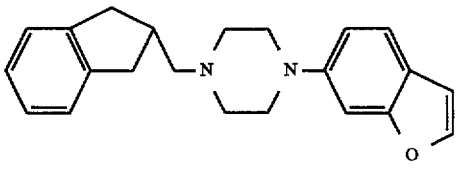

Prepared as described in Example 31 but in Step 1 using 4-(benzofuran-6-yl)piperazine. The difumarate of the title compound melts at 168°–170° C. (ethanol).

Preparation of new starting materials

Preparation 1

4-(2,3-Dihydro-5-methoxybenzofuran-6-yl)piperazine

Step 1. 2,3-Dihydro-5-methoxy-6-nitrobenzofuran 15 g (100 mmol) of 2,3-dihydro-5-methoxybenzofuran dissolved in 15 ml of glacial acetic acid are added dropwise at 0° C., over a period of 15 minutes, to 18.7 ml of fuming nitric acid in 37.5 ml of water. The whole is stirred for 1 hour at 0° C. and then for 1 hour 30 minutes at room temperature. The reaction mixture is poured into 125 ml of water, and the resulting solid is filtered and washed abundantly with water. After drying, 16.9 g of the expected product are obtained (yield=87%). M.p.=108°–109° C.

Step 2. 6-Amino-2,3-dihydro-5-methoxybenzofuran 7.1 g (36.4 mmol) of the compound obtained in the preceding Step in 100 ml of methanol containing 100 mg of platinium oxide are hydrogenated at room temperature and ordinary pressure for 3 hours. After filtering off the catalyst and evaporating off the solvent, 5.85 g of the expected amine are obtained in the form of an oil (yield=97%).

Step 3. Title compound 5.75 g (34.8 mmol) of the amine obtained above, 6.2 g (34.8 mmol) of bis(2-chloroethyl)amine hydrochloride and 4.81 g (34.8 mmol) of potassium carbonate dissolved in 90 ml of chlorobenzene are heated at reflux for 22 hours. The whole is poured into water and the chlorobenzene is decanted off. The aqueous phase is rendered basic with 12 ml of concentrated sodium hydroxide solution and extracted twice with 250 ml of ethyl acetate each time. The organic phases are washed with 250 ml of a saturated NaCl solution. After drying, 5.95 g of the expected product, purified in the form of its hydrochloride, are obtained. M.p.>260° C.

Preparation 2

4-(2,3-Dihydrobenzo-1,4-dioxin-6-yl)piperidine

Step 1. Magesium compound of 6-bromo-2,3-dihydrobenzo-1,4-dioxin 10 g (46 mmol) of 6-bromo-2,3-dihydrobenzo-1,4-dioxin dissolved in 100 ml of THF are added rapidly to a suspension of 1.1 g (0.046 g.atom) of magnesium in 20 ml of THF. The reaction is started by heating in the presence of an iodine crystal and a few drops of methyl iodide. When the addition is complete (approximately 15 minutes), the whole is heated at reflux for 1 hour. A perfectly clear solution is obtained.

Step 2. 1-Benzyl 4-(2,3-dihydrobenzo-1,4-dioxin-6-yl)-4-hydroxypiperidine 6.9 g (37 mmol) of N-benzylpiperid-4-one dissolved in 80 ml of THF are added at 0° C. to the solution of Grignard reagent obtained above. When the addition is complete, the whole is stirred at room temperature for 2 hours, then hydrolysed with a saturated NH$_4$Cl solution. The whole is concentrated to dryness and then the residue is taken up in ether and extracted with 1N HCl. The acidic phase is rendered basic with N sodium hydroxide solution and then extracted with ether. That ethereal phase is dried and then evaporated to dryness. 8 g of the expected product (yield=67%) are obtained. M.p.=154°–156° C.

Step 3. 1-Benzyl-4-(2,3-dihydrobenzo-1,4-dioxin-6-yl)-1,2,3,6-tetrahydropyridine 4 g (12.3 mmol) of the product obtained in Step 2 are added to 50 ml of trifluoroacetic acid. The whole is heated for 30 minutes at 60° C., cooled and neutralised with 35% sodium hydroxide solution. Extraction is carried out with ether and the extract is washed with water, dried over MgSO$_4$, filtered and evaporated to dryness. The residue obtained is purified by chromatography on silica (eluant: CH$_2$Cl$_2$/CH$_3$OH: 95/5). 1.5 g of the desired product are obtained in the form of an oil (yield=40%).

Step 4. Title compound 3.2 g (10.4 mmol) of the product obtained in Step 3 are dissolved in 150 ml of ethanol. 1.5 g of 20% Pd(OH)$_2$ on carbon are added and the whole is hydrogenated at room temperature for 24 hours under a pressure of 4×10$^5$ Pa. The catalyst is filtered off and the filtrate is evaporated to dryness. 1.7 g of the expected product are obtained in the form of an oil (yield=77%).

Preparation 3

4-(2,3-Dihydrobenzo-1,4-dioxin-6-yl)1,2,3,6-tetrahydropyridine 2 g (6.5 mmol) of the compound obtained in Step 3 of Preparation 2 are dissolved in 30 ml of 1,2-dichloroethane. 1.2 ml (13 mmol) of ethyl chloroformate are added and then the whole is heated at reflux for 2 hours, cooled and evaporated to dryness. The residue is taken up in 30 ml of ethanol and 0.7 g (13 mmol) of potassium hydroxide and then heated at reflux for one night. The whole is cooled, 20 ml of water and a further 1.05 g (19.5 mmol) of potassium hydroxide are added, and the whole is heated at reflux again for two days. After evaporation of the ethanol, the mixture is diluted with water and extracted with ethyl acetate, dried over $MgSO_4$, filtered and evaporated to dryness to yield 1.4 g of the title compound (yield: 100%).

Preparation 4

4-(2,3-Dihydro-5-ethoxybenzofuran-6-yl)piperazine

Obtained in the same manner as the product of Preparation 1 but with the replacement in Step 1 of 2,3-dihydro-5-methoxybenzofuran with 2,3-dihydro-5-ethoxybenzofuran. Maroon solid (m.p.=68°–69° C.)

Preparation 5

4-(2,3-Dihydro-7-methoxybenzo-1,4-dioxin-6-yl)piperazine

Obtained in the same manner as the product of Preparation 1 but with the replacement in Step 1 of 2,3-dihydro-5-methoxybenzofuran with 2,3-dihydro-7-methoxybenzo-1,4-dioxin. The hydrochloride of the title compound melts at: 180°–182° C.

Preparation 6

4-(8-Methoxybenzo-1,5-dioxepin-7-yl)piperazine

Obtained in the same manner as the product of Preparation 1 but with the replacement in Step 1 of 2,3-dihydro-5-methoxybenzofuran with 8-methoxybenzo-1,5-dioxepin. The hydrochloride of the title compound melts at 187°–189° C.

Preparation 7

Cyclopenta[c]thien-5-ylcarboxylic acid

Step 1: Cyclopenta[c]thiophene-5,5-dicarboxylic acid diethyl ester

At room temperature, 4.5 g (15.0 mmol) of 3,4-bis-(bromomethyl)thiophene (the synthesis of which is described in J. Prakt. Chem. 1972, 314(2), 334–352), 2.3 ml (15.0 mmol) of diethyl malonate, 4.3 g (31.0 mmol) of potassium carbonate and 75 ml of methyl ethyl ketone are mixed together. The whole is heated at reflux for 20 hours, then evaporated to dryness, taken up in 200 ml of dichloromethane and washed twice with 50 ml of water each time. After drying over magnesium sulphate, then evaporation, the residue is chromatographed on silica (eluant:dichloromethane) to yield 1.8 g of the desired compound (yield: 45%).

Step 2: Cyclopenta[c]thiophene-5,5-dicarboxylic acid

A solution of 2.2 g (38.8 mmol) of potassium hydroxide in 2.2 ml of water is added in one go to 2.6 g (9.7 mmol) of the above compound in 5 ml of ethanol. The whole is heated at reflux for 6 hours and then evaporated to dryness. The residue is taken up in 50 ml of N hydrochloric acid and extracted 3 times with 80 ml of ether each time. The combined ethereal phases are dried over magnesium sulphate and then concentrated to yield 1.85 g of the desired compound (yield: 88%).

Step 3: Cyclopenta[c]thien-5-ylcarboxylic acid 1.8 g (8.5 mmol) of the above compound in 8.5 ml of N,N-dimethylacetamide is heated at reflux for 1 hour. The whole is then evaporated to dryness and subsequently taken up in 100 ml of ether and washed 4 times with 50 ml of water each time. After drying over magnesium sulphate, then evaporation, 1.32 g of the desired compound are obtained (yield: 94%).

Preparation 8

Cyclopenta[b]thien-5-ylcarboxylic acid

Step 1: Methyl 3-(thien-3-yl)-3-oxopropanoate 24 g (0.6 mmol) of sodium hydride (60%) are added in portions at 0° C., over a period of 10 minutes, to 25.2 g (0.2 mmol) of 3-acetylthiophene in 600 ml of dimethyl carbonate, and then the whole is heated at reflux for 30 minutes, allowed to cool and poured into 1 liter of a water/ice mixture containing 53 ml of acetic acid. Extraction is carried out 3 times with 250 ml of ether each time. The combined organic phases are dried over magnesium sulphate. After evaporation, the residue is chromatographed on silica (eluant:dichloromethane) to yield 17 g of the desired compound (yield: 46%).

Step 2: 4-Oxocyclopenta[b]thien-5-ylcarboxylic acid methyl ester

At room temperature, 4.9 g (26.6 mmol) of the above keto ester are added to 7.8 g (58.5 mmol) of aluminium chloride in 75 ml of nitromethane and the whole is then stirred for 15 minutes. 2.9 ml (31.9 mmol) of 2-methoxyacetyl chloride in 25 ml of nitromethane are then added dropwise over a period of 10 minutes, and the whole is heated at 80° C. for 3 hours, allowed to cool and poured into 100 ml of an aqueous 10% oxalic acid solution, then extracted 3 times with 100 ml of ether each time. The combined ethereal phases are washed twice with 150 ml of a saturated aqueous sodium hydrogen carbonate solution each time, dried over magnesium sulphate and concentrated, the residue being chromatographed on silica to yield 2.85 g of the desired compound (yield: 55%).

Step 3: Cyclopenta[b]thien-5-ylcarboxylic acid methyl ester

In a mortar, 7 g (107.2 atom-gram) of zinc are intimately mixed with 0.78 g (2.9 mmol) of mereuric chloride, then the whole is stirred vigorously for 10 minutes in 10 ml of water containing 0.3 ml of concentrated hydrochloric acid. The aqueous phase is decanted off and then 6 ml of water, 12 ml of concentrated hydrochloric acid acid and 2.8 g (14.3 mmol) of the above compound in 15 ml of toluene are added in succession. The whole is heated at reflux for 18 hours, then allowed to cool, and the amalgam is separated off and extracted twice with 20 ml of ether each time. The combined organic phases are washed twice with 20 ml of an aqueous 10% sodium carbonate solution each time, dried over magnesium sulphate and concentrated, the residue being chromatographed on silica (eluant:dichloromethane+2% ethyl acetate) to yield 1.15 g of the desired compound (yield: 44%).

Step 4: Cyclopenta[b]thien-5-ylcarboxylic acid 1.05 g (5.8 mmol) of the above compound and 3.5 ml (7 mmol) of 2N sodium hydroxide solution in 6 ml of methanol are stirred at room temperature for 24 hours, then evaporated to dryness, taken up in 50 ml of water, washed twice with 25 ml of ether each time, acidified with N hydrochloric acid and extracted 3 times with 40 ml of ether each time. The combined ethereal phases are dried over magnesium sulphate and concentrated to yield 0.86 g of the desired compound (yield: 88%)

EXAMPLE 30

Pharmacological study

In vitro Determination of the affinitiy for human $D_4$ receptors

Membranes prepared from CHO cells transfected with human $D_4$ receptor were bought from Receptor Biology Inc. (MD, U.S.A.). The membranes are incubated in triplicate with 30 µg of membrane protein, 0.5 mmol of [$^3$H] spiperone and cold ligand in a final volume of 1 ml, for 60 minutes at 25° C. The incubation buffer contains 50 mM Tris-HCl (pH 7.4), 120 mM NaCl, 5 mM KCl, 5 mM $MgCl_2$ and 1 mM EDTA. After incubation, the incubation medium is filtered across WHATMAN GF/B filters impregnated with 0.1% polyethyleneimine, and washed three times with 2 ml of cooled buffer each time. The radioactivity retained on the filters is determined by liquid scintillation counting. The binding isotherms are analysed by an informed non-linear regression method for determining $IC_{50}$ values. They are converted into the inhibition constant ($K_i$) by means of the Cheng-Prusoff equation:

$$K_i = \frac{IC_{50}}{1+L/Kd}$$

in which L is the concentration of free [$^3$H] spiperone and Kd is the [$^3$H] spiperone dissociation constant of the human $D_4$ receptor (70 pM).

The products of the invention have $K_i$ values for the $D_4$ receptor of less than $5 \times 10^{-8}$M.

Determination of the affinity for human $D_2$ receptors

The procedure used here has already been described in detail in the literature. CHO cells are transfected in a stable manner with cDNA coding for human $D_2$ receptor and, for the binding studies, the membranes are incubated with 0.1 nM [$^{125}$I]-iodosulpiride and the specific binding is greater than 90%. The $IC_{50}$ and $K_i$ values are determined and calculated as above. The products of the invention have $K_i$ values for the $D_2$ receptor greater than $10^{-6}$M.

In vivo a) Pharmacological models

Male Wistar rats (Iffa Credo, Illskirchen France) weighing 250 to 280 g are kept in a 12h/12h light/darkness cycle (light switched on at 7.30 a.m.). They have free access to water and food; the laboratory temperature is 21°±1° C. and the humidity is 60±5%.

Dopamine turnover: The effect of the products of the invention and the reference product on dopamine turnover is determined after subcutaneous injection. After a period of 30 minutes, the rats are decapitated and the brain is dissected in order to extract the striatum, the nucleus accumbens, the frontal cortex and the olfactory tubercles. The tissues are homogenised in 500 µl of $HClO_4$ 0.1M containing 0.5% $Na_2S_2O_5$ and 0.5% EDTA $Na_2$ and centrifuged at 15,000 g for 15 minutes at 4° C. The supernatants are diluted in the mobile phase and injected into an HPLC column (Hypersil ODS 5 µm, C18, 150×4.6 mm, Thermo Separation Products, Les Ulis, France) thermostatically controlled at 25° C. The HPLC mobile phase is composed of 100 mM $KH_2PO_4$, 0.1 mM EDTA, 0.5 mM sodium octylsulphonate and 5% methanol adjusted to pH 3.15 with $H_3PO_4$.

The mobile phase is injected with a BECKMAN 116 pump and at a flow rate of 1 ml/min. The electrochemical detection is carded out by a Waters M460 detector of which the potential of the working electrode is 850 mV relative to an Ag/AgCl reference. The quantities of dopamine and of dihydroxyphenylacetic acid (DOPAC), a metabolite of dopamine, are expressed in relation to the amount of proteins contained in the removed cerebral structure. Bovine serum albumin (Sigma Chemical Co, St-Louis, Mo.) is used as the reference. The DOPAC/dopamine ratio is calculated and is used as the turnover index. For each experiment the ratio between the average amount (±SD) of dopamine and of DOPAC is determined by comparison with the values obtained in the case of the amimals treated with the carrier (100%).

The activity of the products of the invention and of the reference product is expressed in relation to that control value and is reported by way of example in the following Table.

| Products | Dose (mg/kg) | DA: DOPAC ratio (% ± SD) | | | |
| --- | --- | --- | --- | --- | --- |
| | | Frontal cortex | Nucleus accumbens | Olfactory tubercles | Striatum |
| Carrier | — | 100.0 ± 18.2 | 100.0 ± 7.8 | 100.0 ± 7.7 | 100.0 ± 2.2 |
| Haloperidol | 0.63 s.c | 232.1* ± 8.3 | 358.5* ± 15.6 | 298.5* ± 8.9 | 371.5* ± 17.8 |
| Example 6 | 40.0 s.c | 153.0* ± 10.4 | 147.1* ± 9.5 | 125.2* ± 1.6 | 139.3* ± 8.4 |
| | 160.0 p.o | 167.2* ± 16.1 | 195.4* ± 18.3 | 155.2* ± 8.8 | 197.1* ± 15.3 |

N ≧ 5 per value.
*p ≦ 0.05 vs carrier

Those results show that, like haloperidol, the compounds of the invention have a significant effect on dopaminergic transmission in each of the regions studied, indicating a good activity in vivo and a good bioavailability by the oral route.

Dialysis: Rats are anaesthetised with pentobarbital (60 mg/kg i.p.). They are placed in a Kopf stereotaxic device and cannula guides (intracerebral guides, Carnegie Medicine, Stockholm, Sweden) are implanted either in the striatum and the contralateral nucleus accumbens or in the cingulate frontal cortex in accordance with the respective coordinates described as follows in the Paxinos and Watson atlas (1982): nucleus accumbens (CMA/12, AP:+1.6, L:±1.4, DV:−5.7); striatum (CMA/12, AP:+0.5, L:±2.8, DV:−3) and cingulate frontal cortex (CMA/11, AP:+2.2, L:±0.6, DV:−0.2). The rats are placed in separate cages and are not used in dialysis until 5 days later. On the day of the dialysis, CMA/12 probes made of polycarbonate (striatum: 3 mm long, 0.5 mm external diameter, nucleus accumbens: 2 mm long, 0.5 mm external diameter) and CMA/11 probes made of cuprophan (cingulate frontal cortex: 4 mm long, 0.24 mm external diameter) are slowly lowered and held in position. Those probes are perfused at a flow rate of 1 ml/min with a solution of 147.2 mM NaCl, 4 mM KCl and 2.3 mM $CaCl_2$ adjusted to pH 7.3 with a phosphate buffer (0.1M). Two hours after implantation, samples are collected every 20 minutes for 4 hours. Three base samples are taken before administration of the products to be tested. The rats are left in their individual cages for the whole of the experiment. When the experiment is finished, the rats are decapitated and the brain is removed and frozen in cold isopentane. Sections of a thickness of 100 µm are cut and coloured with cresyl violet, which allows verification of the location of the probes.

The simultaneous quantification of dopamine, norepinephrine and serotonin is carried out as follows: 20 µl of dialysis samples are diluted with 20 gl of mobile phase ($NaH_2PO_4$: 75 mM, EDTA: 20 µM, sodium dodecanesulphonate: 1 mM, methanol: 17.5%, triethylamine: 0.01%, pH: 5.70) and 33 µl are analysed by HPLC with a reverse phase column (Hypersil ODS 5 µm, C18, 150×4.6 mm, Thenno Séparation Products, les Ulis, France), which is thermostatically controlled at 45° C., and quantified by means of a coulometric detector (ESA 5014, Coulochem II, Bedford, Mass., U.S.A.). The potential of the first electrode of the detector is set at −90 mV (reduction) and the second at +280 mV (oxidation). The mobile phase is injected with a Beckman 116 pump at a flow rate of 2 ml/min. The sensitivity limits for dopamine, norepinephrine and serotonin are 0.55 fmole per sample. All the products of the invention and the reference substance are injected by the subcutaneous route in a volume of 1.0 ml/kg. The products are dissolved in distilled water to which a few drops of lactic acid have been added if necessary. The quantities of neurotransmitters are expressed as a function of the average of the 3 base values. A variance analysis, with the time factor as repeated measurement, followed by a Newman-Keuls test ($p<0.05$) is employed for the statistical evaluation of the effects of the products. The activity of the products of the invention and of the reference product is expressed by the percentage variation of the quantity of neurotransmitter after administration of the products compared with the base value (=100%).

By way of example, the changes recorded in respect of the quantity of dopamine are given in the Table below.

| | | Average ± SD in % | | |
|---|---|---|---|---|
| Products | Dose (mg/kg) | Frontal cortex | Nucleus accumbens | Striatum |
| Carrier | — | 100.0 ± 14.3 | 100.0 ± 8.9 | 100.0 ± 5.6 |
| Haloperidol | 0.63 s.c. | 148* ± 9 | 133* ± 7 | 129* ± 7 |
| Example 6 | 40.0 s.c. | 201* ± 12 | 103* ± 6 | 104* ± 8 |

N ≧ 5 per value   * p ≦ 0.05 vs carrier

Those results show that, contrary to the reference product, the products of the invention increase mesocortical dopaminergic transmission. That effect shows that the products of the invention enable more effective control of the deficient symptoms of schizophrenia and also have anti-depressant and pro-mnesic propertieis.

b) Therapeutic models

1. Verticalisation induced by apomorphine (0.75 mg/kg, s.c.) in the mouse

This test, described by Protais et al (Psychopharmacologie, 1976, 50, 1–6) allows the evaluation of the dopaminergic antagonist activity of possible antipsychotic products. A mouse to which apomorphine has been administered and which has been placed in a cage comprising vertical bars, remains most of the time immobile at the top of the cage clinging by its 4 paws to the bars. That verticalisation behaviour is blocked if a dopaminergic antagonist product has been administered before the apomorphine.

Test: After the subcutaneous (s.c.) administration of the product or solvent (control group), the mouse is placed in a cylindrical barred cage (14 cm diam.×14 cm h) having vertical bars. Thirty minutes later, the animal receives the apomorphine dose (0.75 mg/kg, s.c.). The animals are observed 10 and 20 minutes after the injection of apomorphine and are given a score 0 (4 paws on the ground), a score 1 (mouse upright with the two front paws on the bars) or a score 2 (mouse clinging by its 4 paws to the bars) each time a measurement is taken. The verticalisation score used for the results is from 0 to 4 (the sum of two measurements). Each experimental group comprises at least 5 animals.

Statistical analysis: The effect of the product on verticalisation is evaluated by comparing the scores obtained for each group that has been administered a dose of product with those obtained for the control group (solvent) using a Mann and Whitney U test, with a probability $p<0.05$. The $ID_{50}$ is that dose of product which reduces by half the average of the verticalisation scores compared with that of the control group.

Results: As an example, and in order to illustrate the effect of the products of the invention, the $ID_{50}$ for the compound of Example 6 is 3.88 mg/kg by the subcutaneous route.

2. Test of aggressiveness in isolated mice

This test allows the evaluation of the intraspecies antiaggressive activity of a product in mice that have been kept in isolation for several months.

Animals: The test uses male CD mice (Charles River) weighing from 22 to 25 g when they arrive at the animal house. On their arrival, the animals are isolated in individual cages made of opaque black polycarbonate (23×14×13 cm) with a grill lid, and are housed for a prolonged period (approximately 6 months) in the experimentation room.

Selection of pairs of mice: The selection of aggressive pairs of mice that will be used chronically in the study commences after the animals have been isolated for one month. Once or twice per week a mouse from another cage (intruder) is placed in the cage of a (resident) mouse and the two animals are observed to see if they attack one another (sniffing, pursuing, nipping, biting) during that trial. At the end of the trial (maximum duration 10 minutes), each mouse is isolated again in its own cage. If attacks have occurred, the same pair of mice will be tested again in the next trial; if there have been no attacks, each mouse of that pair will be placed in the presence of another mouse in the subsequent trial. Thus, in the course of successive trials carried out at a rate of 1 or 2 per week, definitive pairs of mice that will be used for the experiments are selected. The selection of the pairs is based on the stability of the combative nature of the animals from one trial to the next, the shortness of the latent period of the first attack and the frequency and duration of the attacks. With the pairs selected in that manner, those parameters are checked each week by a rapid trial, without treatment, two days before the Test day.

Test: The test takes place once a week. Thirty minutes before being placed together, the two mice of the pair each receive the same treatment (product or solvent) and remain isolated in their respective cages. At TO min., the intruder mouse is introduced into the cage of the resident mouse for a period of 3 minutes. The latent period (in seconds) of the first attack and the number and total duration (in seconds) of the attacks are recorded. A possible reversal of the dominance of one mouse in relation to the other is also noted (in general, the resident mouse is the dominant mouse).

At the end of the test, the intruder mouse returns to its cage; the animals remain in isolation until the next rapid trial and test the following week.

Statistical analysis: The effects of a product on aggressiveness are evaluated by comparing the number and the duration of the attacks by the pairs of mice that have received the product (treated groups) with those obtained with the pairs that have received the solvent (control group) by using a variance analysis (ANOVA) followed by a Dunnett's test, with the probability p<0.05.

The $ID_{50}$ of the number or the duration of the attacks is that dose of the product which reduces by half the average of each of those values compared with those obtained respectively in the control group.

Results: As an example, and in order to illustrate the activity of the products of the invention, the $ID_{50}$ for the compound of Example 6 is 0.99 mg/kg by the subcutaneous route.

3. Induction of catalepsy in the rat

The prolonged administration of "typical" neuroleptics or antipsychotics (haloperidol, chlorpromazine) to schizophrenia patients often brings about the appearance of undesirable extrapyramidal symptoms (EPS) of the Parkinson's type, in particular an immobility phenomenon (Davis et al., 1983). By way of contrast, "atypical" antipsychotics (clozapine) cause few extrapyramidal symptoms.

The acute administration of "typical" antipsychotics to an animal induces catalepsy, that is to say the maintenance of the animal in an often abnormal posture which has been imposed upon it by the experimenter (Waldmeier, 1979). The evaluation of the cataleptogenic properties of a product in the rat thus makes it possible to know whether that product, administered to man, will or will not risk causing an extrapyramidal-type syndrome.

Test: The animals are placed in individual cages and food is withdrawn the day before the test but water taken as desired. The catalepsy test comprises placing each rear paw of the animal on the front paw of the same side and measuring the time (seconds) that the animal remains in that "crossed paws" position (maximum 30 seconds). Each animal is subjected to 3 successive tests (one every two minutes), the animal being removed from its cage and placed on the work surface. Those tests are carded out 1 hour after the subcutaneous injection or oral administration of the product or its solvent. The average value of 3 tests represents the duration of the catalepsy (seconds) for each animal. There are 5 or 6 rats per experimental group.

Statistical analysis: The effect of the product on the duration of the catalepsy is evaluated by an ANOVA, followed by a Dunnett's test, with the probability p<0.05.

The $ED_{50}$ of cataleptsy induction is that dose which causes a catalepsy of a duration of 50% compared with the maximum value of 30 seconds (corrected by the value of the solvent control group).

Results: As an example and in order to illustrate the absence of a cataleptogenic effect of the compounds of the invention, the compound of Example 6 has an $ED_{50}$ greater than 80 mg/kg by the subcutaneous route. By comparison, haloperidol, the reference antipsychotic, has an $ED_{50}$ of 0.146 mg/kg by the same route. This result shows the great value of a selective blockade of $D_4$ receptors compared with $D_2$ receptors in avoiding the extrapyramidal-type side effects encountered with antipsychotics that have a mechanism of action based, inter alia, on a blockade of $D_2$ receptors.

We claim:

1. A compound selected from those of formula I:

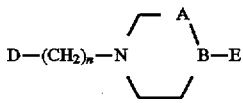

(I)

wherein

A-B is selected from the group consisting of: $CH_2$—CH and CH=C, n is selected from the group consisting of zero and 1 to 6 inclusive, D represents one of the following bicyclic systems:

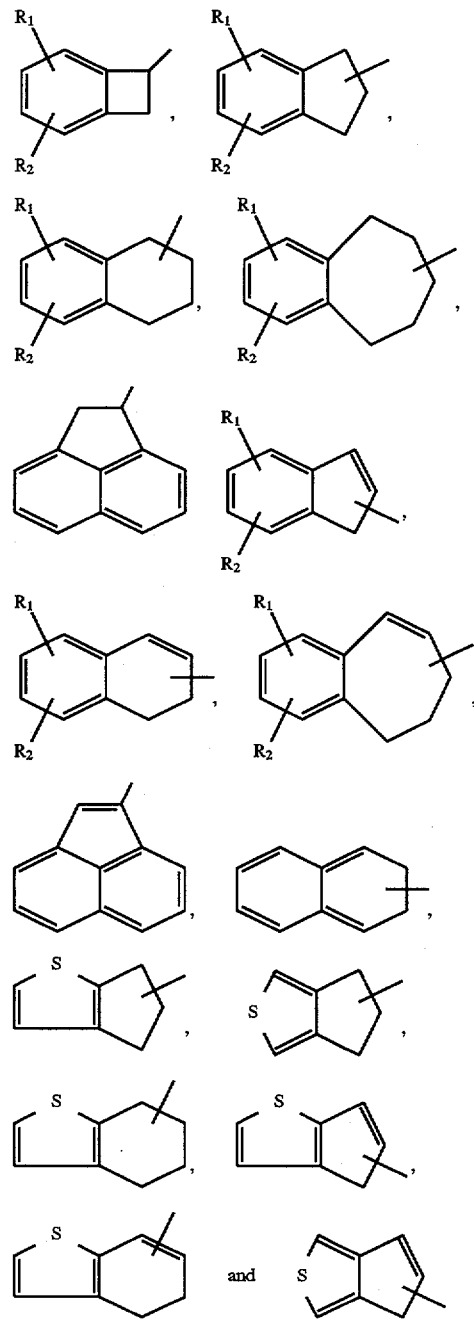

wherein:

$R_1$ and $R_2$, which are identical or different, are each selected from the group consisting of hydrogen, halogen, straight-chain and branched alkyl and alkoxy each having 1 to 5 carbon atoms inclusive, and hydroxy; and E represents one of the following heterocycles:

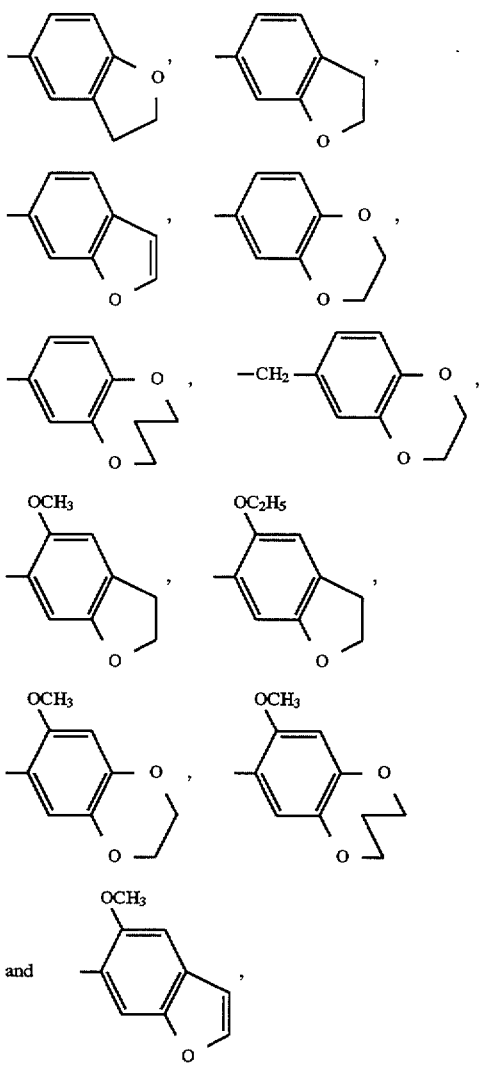

with the proviso that E does not represent:

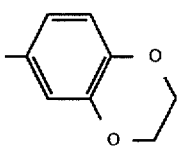

when D is

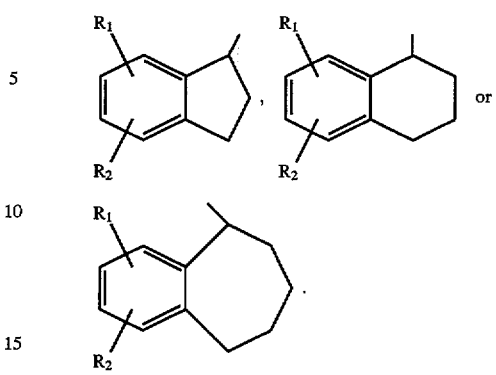

its racemic mixtures or racemates and optical isomers or enantiomers
and salts thereof with a pharmaceutically acceptable acid.

2. A new intermediate product selected from those compounds of formula V:

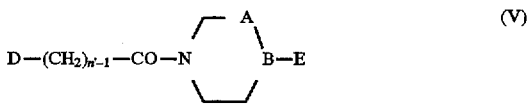

wherein

A—B, D, and E are as defined in claim 1 and n' is 1 to 6 inclusive.

3. A method for treating a living animal body afflicted with a condition associated with a dysfunction of the dopaminergic system, comprising the step of administering to the living animal body an amount of a compound of claim 1 which is effective for alleviation of said condition.

4. A pharmaceutical composition acting as D4 receptor ligand and useful in the alleviation of a dopaminergic system dysfunction, comprising as active ingredient at least one of the compounds according to claim 1, together with one or more pharmaceutical excipients.

5. A compound of claim 1 selected from the group consisting of 4-(2,3-dihydrobenzo-1,4-dioxin-6-yl)-1-(indan-2-ylmethyl)piperidine and its dihydrochloride.

6. A compound of claim 1 selected from the group consisting of 4-(2,3-dihydrobenzo-1,4-dioxin-6-yl)-1-[(indan-2-yl)methyl]-1,2,3,6-tetrahydropyridine and its fumarate.

* * * * *

UNITED STATES PATENT AND TRADEMARK OFFICE
CERTIFICATE OF CORRECTION

PATENT NO. : 5,684,020
DATED : Nov. 4, 1997
INVENTOR(S) : J.L. Peglion, A. Dessinges, B. Goument, M. Millan, A. Newman-Tancredi It is certified that error appears in the above-indentified patent and that said Letters Patent is hereby corrected as shown below:

Column 11, line 26: Delete the "[" at the end of the line.

Column 11, line 27: Insert -- [ -- at the beginning of the line.

Column 25, line 38: "carded" should read -- carried --.

Column 28, line 21 (approx.): Insert a -- hyphen -- between "pharmaceutically" and "acceptable".

Signed and Sealed this

Third Day of February, 1998

Attest:

Attesting Officer

BRUCE LEHMAN

Commissioner of Patents and Trademarks